(12) United States Patent  
Guarnaccia

(10) Patent No.: US 8,664,209 B2  
(45) Date of Patent: Mar. 4, 2014

(54) DAPTOMYCIN FOR MULTIPLE SCLEROSIS

(76) Inventor: Joseph B. Guarnaccia, Derby, CT (US)

( * ) Notice: Subject to any disclaimer, the term of this patent is extended or adjusted under 35 U.S.C. 154(b) by 0 days.

(21) Appl. No.: 13/395,369

(22) PCT Filed: Sep. 2, 2010

(86) PCT No.: PCT/US2010/002439
§ 371 (c)(1),
(2), (4) Date: Apr. 17, 2012

(87) PCT Pub. No.: WO2011/043788
PCT Pub. Date: Apr. 14, 2011

(65) Prior Publication Data
US 2012/0202746 A1   Aug. 9, 2012

Related U.S. Application Data

(60) Provisional application No. 61/248,496, filed on Oct. 5, 2009, provisional application No. 61/249,639, filed on Oct. 8, 2009, provisional application No. 61/263,779, filed on Nov. 23, 2009.

(51) Int. Cl.
*A61K 31/585* (2006.01)
(52) U.S. Cl.
USPC ........................................................ 514/175
(58) Field of Classification Search
None
See application file for complete search history.

*Primary Examiner* — John Ulm
(74) *Attorney, Agent, or Firm* — Edwards Wildman Palmer LLP; Peter F. Corless; Richard B. Emmons

(57) ABSTRACT

Compounds and compositions, and methods of use thereof, for treatment and/or prevention of multiple sclerosis, including symptoms associated with multiple sclerosis, and/or treatment and/or prevention of other disease/disorder affecting the nervous system (e.g. central, peripheral) or muscle including symptoms thereof, comprising administering to a subject in need thereof daptomycin and/or daptomycin-related lipopeptide.

15 Claims, No Drawings

DAPTOMYCIN FOR MULTIPLE SCLEROSIS

CROSS-REFERENCE TO RELATED APPLICATION

This application is the U.S. national phase under 35 U.S.C. §371 of PCT International Application No. PCT/US2010/002439, filed Sep. 2, 2010, which claims the benefit of the following U.S. Provisional Application Nos. 61/248,496, filed Oct. 5, 2009, 61/249,639, filed Oct. 8, 2009, and 61/263,779, filed Nov. 23, 2009, the entire contents of each of which are incorporated herein by reference.

BACKGROUND OF THE INVENTION

Multiple sclerosis (MS) is generally known as an autoimmune disease of the central nervous system with both autoimmune and neurodegenerative features. It affects approximately 400,000 persons in the United States and 1.2 million persons worldwide. It is a major cause of neurological disability in young adults, who usually present with a relapsing, remitting pattern of neurologic involvement and progress to a chronic phase with increasing difficulty in ambulation and coordination. Studies have shown that nearly fifty percent of MS patients require an assistive device to walk after a decade of disease. Therefore, the societal impacts of both direct medical and indirect economic costs of MS are enormous and often imposed on young families.

Currently used drugs/agents for MS treatment either modify or suppress the body's immune system. They have been shown to modestly reduce neurological relapses of the disease and, in some instances, incompletely slow the progression of neurological disability. However, the vast majority of currently used drugs/agents for MS are variously limited by incomplete efficacy, side effects and medical risks, e.g., injection site reactions, including skin necrosis; flu-like symptoms; depression; psychosis; hypersensitivity; allergic reactions; cardiac and other organ toxicity from diabetes mellitus; cataracts; bone necrosis; serious and life threatening opportunistic infections, and risk of malignancy. The existence of these side effects and risks precludes the use of these drugs in many MS patients. Thus, there is a pressing need for therapeutic approaches/agents that are safe, efficacious, well-tolerated, and which can be administered more conveniently.

SUMMARY OF THE INVENTION

The invention relates to compounds and compositions, and methods of use thereof, for treatment and/or prevention of multiple sclerosis, including symptoms associated with multiple sclerosis, and/or treatment and/or prevention of other disease/disorder affecting the nervous system (e.g. central, peripheral) or muscle including symptoms thereof, comprising administering to a subject in need thereof daptomycin and/or daptomycin-related lipopeptide.

The invention is based, at least in part, on the discovery of the beneficial effects of daptomycin in a subject with multiple sclerosis. Accordingly, the invention provides for the use of daptomycin for treatment and/or prevention of multiple sclerosis including symptoms associated with multiple sclerosis. While, currently daptomycin is approved by the FDA for the treatment of complicated skin and skin structure infections caused by certain gram positive microorganisms, its beneficial effects on multiple sclerosis were hitherto unknown.

In one aspect, the invention relates to a method of treating and/or preventing multiple sclerosis, including symptoms associated with multiple sclerosis, comprising administering daptomycin to a subject in need thereof. The composition comprising daptomycin may optionally contain at least one daptomycin-related lipopeptide and/or known MS drug(s)/agent(s), and/or or may be administered in combination with at least one daptomycin-related lipopeptide and/or known MS drug(s)/agent(s).

In another aspect, the invention relates to a method of treating and/or preventing a disease/disorder affecting the nervous system (e.g. central, peripheral) or muscle, including treating and/or preventing symptoms thereof, comprising administering daptomycin to a subject in need thereof. In certain aspects, the disease/disorder affecting the nervous system is other than MS. The composition comprising daptomycin may optionally contain at least one daptomycin-related lipopeptide and/or known MS drug(s)/agent(s), and/or or may be administered in combination with at least one daptomycin-related lipopeptide and/or known MS drug(s)/agent(s).

In yet another aspect, the invention relates to an article of manufacture such as a packaged product containing any of the compositions described herein and a label and/or instructions for use in treating and/or preventing multiple sclerosis, including symptoms associated with multiple sclerosis, and/or or other disease/disorder affecting the nervous system (e.g. central, peripheral) or muscle including symptoms thereof.

In a further aspect, the invention relates to a method of manufacturing an article of manufacture comprising any of the compositions described herein, packaging the composition to obtain an article of manufacture and instructing, directing or promoting the use of the composition/article of manufacture for any of the uses described herein. Such instructing, directing or promoting includes advertising.

In various embodiments of the invention delineated herein, the composition is administered for a duration sufficient to ameliorate multiple sclerosis or symptoms associated with multiple sclerosis (e.g., daily for 1-6 weeks, 1-6 months, or longer (e.g., 1, 2, 3, 5 years or for the life of the patient).

By "ameliorate" is meant decrease, suppress, attenuate, diminish, arrest, or stabilize the development or progression of a disease.

By "analog" is meant a molecule that is not identical, but has analogous functional or structural features. For example, a daptomycin analog retains the biological activity of daptomycin, while having certain modifications that enhance the analog's function relative to the reference compound. Such modifications could increase the analog's oral availability, or half-life.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "disease" is meant any condition or disorder that damages or interferes with the normal function of a cell, tissue, or organ. Examples of diseases include multiple sclerosis.

By "reference" is meant a standard or control condition.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

DETAILED DESCRIPTION

The invention relates to compounds and compositions, and methods of use thereof, for treatment and/or prevention of multiple sclerosis, including symptoms associated with multiple sclerosis, and/or other disease/disorder affecting the nervous system (e.g. central, peripheral) or muscle including symptoms thereof, comprising administering to a subject in need thereof daptomycin and/or a daptomycin-related lipopeptide. Use of the pharmaceutically acceptable salts of daptomycin and/or a daptomycin-related lipopeptides is also within the scope of the invention.

The invention is based, at least in part, on the discovery that daptomycin provided dramatic and sustained functional improvement, first, in a 53 year old woman with secondary progressive multiple sclerosis (SPMS) poorly responsive to other therapies. These promising results prompted the use of daptomycin in 30 other patients with progressive and relapsing forms of multiple sclerosis who were similarly unresponsive to multiple therapies. Surprisingly, 47% of patients treated with daptomycin showed clinically significant improvement in symptoms of multiple sclerosis.

Daptomycin refers to a compound described by the chemical name: N-decanoyl-L-trypotophyl-D-asparaginyl-L-aspartyl-L-threonylglycyl-L-ornithyl-L-aspartyl-D-alanyl-L-aspartylglycyl-D-seryl-threo-3-methyl-L-glutamyl-3-anthraniloyl-L-alanine ∊1-lactone. Daptomycin, also known as LY 146032, is a cyclic lipopeptide antibiotic, derived from the fermentation of *Streptomyces roseosporus*, and is approved by the FDA for the treatment of complicated skin and skin structure infections caused by susceptible isolates of gram positive microorganisms, including methicillin-resistant *Staphylococcus aureus* (MRSA) and vancomycin-sensitive *Enterococcus faecalis* (VRE) and bloodstream infections caused by methicillin-susceptible and methicillin-resistant strains of *Staphylococcus aureus*. Daptomycin is a member of the A-21978$C_0$ type of antibiotics of *Streptomyces roseosporus* and is comprised of a decanoyl side chain linked to the N-terminal tryptophan of a 13-amino acid peptide. Daptomycin is described by Baltz in: Biotechnology of Antibiotics. $2^{nd}$ Ed., ed. W. R. Strohl (New York: Marcel Dekker, Inc.) 1997, pp. 415-435. Methods for preparing daptomycin are well-known in the art, for e.g., as described in U.S. Pat. No. 6,696,412 and WO/2002/056829, which is hereby incorporated herein by reference with respect to sections describing the methods of preparation. Also hereby incorporated herein by reference are compounds and methods of making disclosed in the U.S. Pat. Nos. 4,482,487; 4,537,717; 4,800,157; 4,874,843; 4,885,243; 5,573,936; 5,629,288; 5,912,226; 6,716,962; 6,696,412; 6,767,718; 6,794,490; 6,911,525; 7,125,844; 7,138,487; 7,241,866; 7,335,725; 7,335,726; 7,408,025; 7,527,807.

As used herein, "daptomycin-related lipopeptide" refer to lipopeptide compounds (e.g., with antibacterial effects) structurally similar to daptomycin, that comprise a proteinaceous domain and a lipid domain. Examples of such compounds include, but are not limited to, members of A-21978 class of compounds (e.g., A-21978C, e.g., A-21978$C_0$), A54145 or A54145 derivatives. Such compounds and methods of their making are known in the art, for example, as described in U.S. Pat. No. 6,696,412, U.S. Pat. No. 6,794,490, and U.S. Pat. No. Re 32, 33, each of which is hereby incorporated herein by reference with respect to their compound and methods of making disclosure.

The invention further provides for the oral administration of daptomycin. Methods for orally administering daptomycin alone, or in combination with other agents that enhance oral availability, are known in the art and described, for example, in the following US Patents, each of which are incorporated herein by this reference: U.S. Pat. Nos. 6,693,208, 6,846,844, 6,900,344, 7,115,663, 7,138,546, 7,151,191, 7,169,776, 7,208,178, 7,217,703, 7,227,033, 7,279,597, 7,390,834, 7,411,084, 7,129,274, 7,495,030.

Other references that may describe the use and administration of daptomycin, and/or daptomycin analogs, include the following: Thompson, "Dosage Regimen Design: A Pharmacokinetic Approach," The Journal of Clinical Pharmacology 32: 210-214, 1992; Voorn et al., "Role of Tolerance in Treatment and Prophylaxis of Experimental *Staphylococcus aureus* Endocarditis with Vancomycin, Teicoplanin, and Daptomycin," Antimicrobial Agents and Chemotherapy 38: 487-493, 1994; Elioppoulos, George M., et al., "In Vitro and In Vivo Activity of LY 146032, a New Cyclic Lipoprotein Antibiotic," Antimicrobial Agents and Chemotherapy 30: 532-535 (1986)' Oleson, F. B., et al., "Once-Daily Dosing in Dogs Optimizes Daptomycin Safety," Antimicrobial Agents and Chemotherapy, 44: 2948-2953 (2000); Richard H. Baltz, "Lipopeptide Antibiotics Produced by *Streptomyces roseosporus* and *Streptomyces fradiae*," Biotechnology of Antibiotics 2d Ed., 415-435, 1997:

Pharmaceutically acceptable salts of daptomycin and daptomycin-related lipopeptides, and their use for the methods described herein, are also within the scope of the invention. Such salts may be prepared using knowledge in the pharmaceutical arts.

In certain embodiments, the present invention relates to a composition comprising an effective amount of at least one of the following: daptomycin, daptomycin-related lipopeptide, a pharmaceutically-acceptable salt thereof and their use in methods described herein.

In additional embodiments, the present invention relates to a composition comprising an effective amount of at least one of the following: daptomycin, daptomycin-related lipopeptide, a pharmaceutically-acceptable salt thereof, in combination with at least one of the following: a drug approved for use for the diseases/disorders recited herein (e.g. for MS); immunoglobulins (synthetic or polyclonal or monoclonal antibodies), immunomodulating drugs (e.g., immunosuppressive, e.g., steroids, e.g. corticosteroids, e.g., cyclophosphamide); antibiotic compound(s); agent or compound(s) which may be of natural origin (e.g., from a plant or animal source), which are beneficial for subjects with multiple sclerosis and/or other disease/disorder affecting the nervous system (e.g. central, peripheral) or muscle.

Methods of Use

The present invention provides methods of treating multiple sclerosis and related diseases and/or disorders or symptoms thereof which comprise administering a therapeutically effective amount of a pharmaceutical composition comprising a compound of the formulae (e.g., daptomycin, daptomycin analogs, daptomycin-related lipopeptides) herein to a subject (e.g., a mammal such as a human). Thus, one embodiment is a method of treating a subject suffering from or susceptible to multiple sclerosis disease or symptoms thereof. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which demyelination may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with multiple sclerosis, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The invention further relates to methods for treatment and/or prevention of multiple sclerosis, including symptoms associated with multiple sclerosis, and/or other disease/disorder affecting the nervous system (e.g. central, peripheral) or muscle including symptoms thereof, in a subject in need thereof using the compounds and compositions described herein. Examples of subjects in need thereof are described below.

Subject within the scope of the present invention is a mammal, such as a human or a veterinary animal, exhibiting symptoms and/or suffering from, or diagnosed with, diseases/disorders described herein. The term "veterinary animal" refers to any animal cared for, or attended to by, a veterinarian, and includes companion (pet) animals and livestock animals, for example, a cat, a dog, and a horse (e.g., a race horse). Other mammals, e.g., such as those used as experimental models for MS, mice, rats, rabbits, nonhuman primates, such as monkeys, are also within the scope of the invention (e.g. experimental allergic encephalomyelitis (EAE)).

Herein, "multiple sclerosis" is used as per the accepted textbook definition in the field (Handbook of Multiple Sclerosis. $3^{rd}$ Edition. Edited by Stuart D. Cook. Marcel Dekker, Inc., 2001). Diagnostic criteria used to identify a subject with multiple sclerosis would be apparent to a person of skill in the art. For example, a skilled individual would appreciate that clinically defined multiple sclerosis is based on two attacks of neurological dysfunction separated in time and space. More recent diagnostic criteria for MS include the presence of characteristic areas on cranial or cervical magnetic resonance imaging (MRI).

Multiple sclerosis frequently begins in young adulthood with episodic attacks of neurological dysfunction, e.g., visual loss, sensory alterations, motor weakness, ataxia, etc. These subjects are within the scope of the present invention. Although the precise cause of multiple sclerosis is largely unknown, it is thought to result from an autoimmune reaction to the protein component of the myelin that forms a sheath-like covering around nerve axons and enhances electrochemical signaling in the central nervous system. Examples of such protein components include, but are not limited to, myelin basic protein, proteolipid protein and myelin oligodendrocyte glycoprotein.

Common symptoms of multiple sclerosis and other diseases/disorders affecting nerves and muscles include, but are not limited to, weakness, muscle stiffness, pain, which can be burning, throbbing, aching, imbalance, asthenia or fatigue, depression, visual disturbances or loss, headache, loss of bowel or bladder control, ataxia of gait or limb movements, difficulty walking, difficulty with coordinated movements of the upper extremities, cognitive dysfunction, loss or aberrant sensation, muscle cramps or spasms, among others. Subject exhibiting these symptoms are within the scope of the present invention.

Certain known subtypes of multiple sclerosis exist that are generally defined by the profile of symptoms exhibited by the subject, including onset, duration, and patterns of neurological dysfunction and/or disability. Subjects suffering from MS subtypes are also within the scope of the invention.

Relapses of multiple sclerosis are discrete occurrences of a subtype of multiple sclerosis known as relapsing remitting multiple sclerosis (RRMS) and occur less often in secondary progressive multiple sclerosis (SPMS). As used herein, a "relapse" is defined as the onset of new or worsening neurological symptoms usually lasting at least 48 hours in the absence of any precipitating factor, such as fever or infection. Subjects suffering from relapses or RRMS are within the scope of the present invention.

Relapses of multiple sclerosis, include but are not limited to, symptoms which may occur alone or in combination of increased or new onset numbness in the trunk or limbs, weakness of the trunk or limbs, imbalance, difficulty walking, reduced or double vision, pain of the face, trunk or extremities, difficulty in urination or bowel movements, sexual dysfunction, cognitive difficulties such as confusion, depression, psychosis or memory loss, vertigo or dizziness, fatigue, and cramps or spasms. Subject exhibiting these symptoms are within the scope of the present invention.

The goal of treatment of relapses is to stop the autoimmune process associated with the relapse and/or to prevent or minimize residual neurological damage associated with incomplete remission, which occurs in a high percentage of patients. There is a significant risk of permanent and severely disabling neurological disability over time, particularly if the disease enters a chronic progressive phase after a relapsing remitting phase (CPMS). Ten percent of patients never experience a relapsing phase prior to a progressive phase and this is termed primary progressive multiple sclerosis (PPMS). There is also a risk that untreated or uncontrolled relapses lead to a state of SPMS, in which progressive neurological disability, including dementia, chronic vertigo, fatigue, visual impairment, motor weakness, sensory disturbances, bladder and bowel dysfunction, ambulation difficulties or non-ambulation, ataxia and pain occur in the absence or reduced frequency of discrete attacks. SPMS and PPMS respond poorly to current drug treatment. Subjects with CPMS and PPMS are also within the scope of the invention.

Examples of subjects with other diseases/disorders affecting the nervous system (e.g. central, peripheral) or muscle, who can benefit from the present invention, include, but are not limited to, subjects with diseases/conditions that affect the peripheral or central nervous system, neuromuscular junction or muscles, e.g., subjects with stroke, Parkinson's disease, Parkinson's syndrome, chronic pain syndromes of unknown etiology, vasculitides of the peripheral or central nervous system, central nervous system sarcoidosis, epilepsy, Guillian-Barré syndrome, neuropathies associated with diabetes mellitus, alcohol abuse, arterial and venous insufficiency, cerebral palsy, myasthenia gravis, myositis, lupus erythematosus, and myelitis. A skilled practitioner would readily appreciate diagnostic criteria and tools available to identify such a subject.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. As used herein, the terms "prevent," "preventing," "prevention," "prophylactic treatment" and the like refer to reducing the probability of developing a disorder or condition in a subject, who does not have, but is at risk of or susceptible to developing a disorder or condition.

In the context of an effective amount, the effect may be therapeutic in terms of improving existing conditions in a multiple sclerosis subject, slowing down or reducing the progression of multiple sclerosis, and/or other disease/disorder affecting the nervous system or muscle (i.e., arresting its development or progression, causing regression of the disease), reducing/ameliorating the risk of progression and/or adverse symptoms/effects attributable to the disease including inflammatory and/or neurological and/or neuromuscular symptoms, and/or inducing a measurable improvement of at least one of the adverse symptoms, and/or inducing a measurable reduction of morbidity associated with the condition/disease/disorder, and/or in prolonging survival.

A person of skill in the art would also appreciate that the terms "prevention" or "preventing" is applicable to multiple sclerosis and/or other disease/disorder affecting the nervous system or muscle. In view of the knowledge that it takes two clinical attacks or episodes to diagnose "clinically definite" MS, a therapy would be considered preventative if, administered after the first episode, which is often called "Clinically Isolated Syndrome" (CIS), it prevents or delays the second episode. In that context, if a subject presents with a clinical attack and an MRI which looks like MS, then the patient is categorized as being at "high risk" of developing clinically definite MS. In the case of such a subject, the first CIS attack and appearance of the MRI are prognostic indicators for relapsing remitting multiple sclerosis (RRMS). The second way in which therapeutic intervention is considered to be preventative is when preventing further attacks of MS. In that respect, most of the well known MS therapies not only reduce the attack rates (in established RRMS) by 30-80%, but also prevent RRMS as well as neurological disability or progression of the disease, albeit to different extents.

A person of skill in the art will be able to determine a suitable route of administration to maximize the delivery of compound and compositions of the invention. These may be administered for example, orally and/or intravenously. Methods of administration of daptomycin and/or daptomycin-related lipopeptides are known in the art and are described e.g., in U.S. Pat. Nos. 6,852,689; 6,468,967; 7,297,794; and U.S. Pat. No. 7,527,807) (the latter two describe e.g., oral administration), each of which is hereby incorporated herein by reference with respect to the routes and dosage/regimen of administration.

The compounds and compositions of the invention may be administered over extended periods of time, as a regimen, e.g., for several days or for several weeks, for example, from two to four weeks, and may be administered, for example, once a day to once a week to once a month, e.g. daily, weekly or monthly for an indefinite period of time. For example, for initial treatment, administration can be carried out daily for a number of days (e.g. 5 to 20 days) and then continued in a once a week, or once a month, regimen for a period of weeks, as needed (e.g. 4 to 12 weeks) or an indefinite period of time.

A daily effective amount of the composition of the invention may be provided, for example, in a single dose. The amount per administered dose, and duration and frequency will depend on factors such as the nature and severity of the condition, age and general health of the subject, the tolerance of the subject to the composition, the response of the disease to therapy and duration and profile of the symptoms experienced by the subject and can be assessed by a person of skill in the art.

The effective amount of daptomycin or a daptomycin-related lipopeptide to be administered according to the methods recited herein may be determined by a person of skill in the art using the guidance provided herein and general knowledge in the art. For example, the effective amount may be such as to achieve a physiologically relevant concentration in the body of a mammal, e.g., human, and/or to achieve any of the therapeutic or prophylactic effects described herein. Relevant doses (expressed as mg per kg of body weight of the human subject) may include from 1 mg/kg and above, e.g. from 2 mg/kg and above, e.g. from 2 mg/kg to 75 mg/kg, e.g. 2 mg/kg to 25 mg/kg, or e.g. 2 mg/kg to 12 mg/kg, e.g., 3 mg/kg, 4 mg/kg or 6 mg/kg intravenously once every 24 hours. Other doses higher than, intermediate to or less than these doses may also be used and may be determined by one skilled in the art following the methods of this invention.

Based on the FDA approval for anti-bacterial uses, daptomycin is generally administered to humans at a dose of 4 mg/kg or 6 mg/kg by intravenous infusion once every 24 hours. For example, for treatment of complicated skin and skin structure infections, daptomycin is administered over a 30 minute period by intravenous infusion at a dose of 4 mg/kg body weight once every 24 hours for 7 to 14 days. For the treatment of bloodstream infections by *Staphalococcus aureus*, including methicillin resistant and methicillin susceptible strains, the dose is 6 mg per kilogram every 24 hours for a minimum of 2 to 6 weeks (Physicians Desk Reference, 2009, Thomson Reuters). These amounts are also relevant for the use in methods described herein.

In one embodiment, daptomycin is administered intravenously once a day, or orally once a day, to a patient with MS who is experiencing an acute attack of disease for three to five days or longer, based on the customary length of time that intravenous or oral corticosteroids are administered. This may, at the discretion of the practitioner, be repeated for incomplete responses. Daptomycin may be administered as initial therapy for relapses in patients who cannot take intravenous steroids because of previous complications from steroids, including but not limited to allergic reactions, psychosis, osteonecrosis of the bone, cataracts or other intolerable side effects, including but not limited to hyperactivity, weight gain or insomnia. Daptomycin may also be administered as a follow on therapy to patients in relapse who have not responded to corticosteroids as initial treatment. Daptomycin-related lipopeptides may also be used.

In another embodiment, daptomycin may be used in patients with MS to stabilize their condition when the patient is experiencing rapid or slow deterioration in their neurological status concomitant with, or in the absence, of relapse. Daptomycin may be administered intravenously on a daily basis, at the discretion of one skilled in the practice of neurology, to be of longer duration, including, but not limited to, five to twenty one days. These patients, typically, have not tolerated other drugs for MS, and/or their disease has not stabilized on these therapies. In this embodiment, intravenous daptomycin, once administered initially as described above to stabilize the patient's neurological deterioration, can be administered intermittently as one dose intravenously every week to once a month as maintenance therapy for an indefinite period. In another embodiment, an initial course, or repeated course, of intravenous daptomycin may be followed by daily oral daptomycin treatment or other oral antibiotic treatment or standard MS therapy as maintenance therapy to prevent further relapses or neurological deterioration for duration of time determined by a neurologist or other physician skilled in the art of treating MS. Daptomycin-related lipopeptides may also be used.

In another embodiment, daptomycin can be used for therapy, e.g., orally or intravenously, to prevent subsequent relapses in patients who present to a physician with a first attack of neurological dysfunction with an MRI scan of the brain, showing areas of abnormality consistent with multiple sclerosis and indicating a high likelihood of conversion to RRMS. This condition is known as Clinically Isolated Syndrome (CIS). In this embodiment, daily oral or intermittent intravenous daptomycin therapy would provide a method of preventing clinically definite MS. Another embodiment includes reducing the risk of and/or mitigating the severity of and delaying the occurrences of clinical attacks of the disease as in RRMS. Daptomycin-related lipopeptides may also be used.

In another embodiment, daptomycin is used in any combination with one or more drugs to ameliorate symptoms of multiple sclerosis to stabilize the disease process and improve quality of life. Such symptomatic drugs are used to treat cognitive dysfunction, fatigue, emotional or psychiatric manifestations, vertigo or dizziness, insomnia, muscle spasticity, weakness and abnormal movements, sensory disturbances, including pain, bladder and bowel dysfunction, seizures, migraine headaches, etc. Daptomycin-related lipopeptides may also be used.

One embodiment relates to the use of daptomycin 3 mg/kg, 4 mg/kg or 6 mg/kg once every 24 hours intravenously and/or the use of a daptomycin-related lipopeptide (or in other dosages and regimens described above) to treat or prevent multiple sclerosis using standard, intermittent durations of therapy.

Another embodiment relates to the use of daptomycin 3 mg/kg, 4 mg/kg or 6 mg/kg once every 24 hours intravenously and/or the use of a daptomycin-related lipopeptide (or in other dosages and regimens described above) using standard, intermittent durations of therapy to treat or prevent related central nervous system inflammatory diseases, including but not restricted to acute demyelinating encephalomyelitis (ADEM) and neuromyelitis optica (NMO).

Another embodiment relates to the use of daptomycin 3 mg/kg, 4 mg/kg or 6 mg/kg once every 24 hours intravenously and/or a daptomycin-related lipopeptide (or in other dosages and regimens described above) using standard, intermittent durations of therapy to treat and/or prevent attacks of multiple sclerosis and other central nervous system inflammatory diseases.

Another embodiment relates to the use of daptomycin 3 mg/kg, 4 mg/kg or 6 mg/kg once every 24 hours intravenously and/or the use of a daptomycin-related lipopeptide (or in other dosages and regimens described above) using standard, intermittent durations of therapy to treat and/or prevent progressive neurological disability from multiple sclerosis and other central nervous system inflammatory diseases.

Another embodiment relates to the use of daptomycin 3 mg/kg, 4 mg/kg or 6 mg/kg once every 24 hours intravenously and/or the use of a daptomycin-related lipopeptide (or in other dosages and regimens described above) using standard, intermittent durations of therapy to treat and/or prevent lesions or plaques on MRI scans of the brain and spinal cord from multiple sclerosis and other central nervous system inflammatory diseases.

Another embodiment relates to the use of daptomycin 3 mg/kg, 4 mg/kg or 6 mg/kg once every 24 hours intravenously and/or the use of a daptomycin-related lipopeptide (or in other dosages and regimens described above) using standard, intermittent durations of therapy to increase quality of life in patients who have multiple sclerosis and other central nervous system inflammatory diseases.

Another embodiment relates to the use of daptomycin 3 mg/kg, 4 mg/kg or 6 mg/kg once every 24 hours intravenously and/or the use of a daptomycin-related lipopeptide (or in other dosages and regimens described above) using standard, intermittent durations of therapy to protect the myelin sheath of central nervous system axons and neurons from demyelination or damage due to inflammation from multiple sclerosis and other central nervous system inflammatory diseases.

Another embodiment relates to the use of daptomycin 3 mg/kg, 4 mg/kg or 6 mg/kg once every 24 hours intravenously and/or the use of a daptomycin-related lipopeptide (or in other dosages and regimens described above) using standard, intermittent durations of therapy to protect neurons from damage or cell death (apoptosis or necrosis) from multiple sclerosis and other central nervous system inflammatory diseases.

Another embodiment relates to the use of daptomycin intravenously by oral administration and/or the use of a daptomycin-related lipopeptide to treat or prevent the symptoms of multiple sclerosis or other neurological or muscular diseases using standard, intermittent durations of therapy, or other dosing regimens consistent with clinical observation and clinical practice.

Another embodiment relates to the use of daptomycin in other formulations or dosing regimens, including oral formulations, as well as other oral daptomycin-related lipopeptide, to treat symptoms of multiple sclerosis and other neurological and muscular diseases.

Another embodiment relates to the use of daptomycin by intravenous or oral administration and/or the use of a daptomycin-related lipopeptide using intermittent or continuous durations of therapy to treat and/or prevent progressive neurological disability from symptoms generally caused by multiple sclerosis and other nerve and muscular diseases or conditions. For example, daptomycin may be given intravenously or orally once a week, once every two weeks or once a month for an indefinite period of time.

Another embodiment relates to the use of daptomycin by intravenous or oral administration and/or the use of a daptomycin-related lipopeptide using intermittent or continuous durations of therapy to increase quality of life in patients who have multiple sclerosis or other nerve and muscular diseases or conditions.

Another embodiment relates to the use of daptomycin by intravenous or oral administration and/or the use of a daptomycin-related lipopeptide using intermittent or continuous durations of therapy to protect neurons from damage or cell death (apoptosis or necrosis) from multiple sclerosis or other nerve and muscular diseases or conditions.

Another embodiment relates to the use of daptomycin by intravenous or oral administration and/or the use of a daptomycin-related lipopeptide using intermittent or continuous durations of therapy to minimize skeletal myopathy or other adverse neuromuscular effects.

The invention is further described in the following non-limiting examples.

EXAMPLES

Example 1

The novel use of daptomycin in the treatment and/or prevention of multiple sclerosis in mammals, particularly human, is based on the recent observation of a patient (Patient A) with multiple sclerosis whose progressive neurological disability stabilized after treatment with daptomycin for skin infections caused by methicillin resistant *Staphalococcus aureus*. Previously, her neurological disability had progressed despite treatment with standard FDA approved therapies as well as investigational therapies, some of which she developed severe allergic reactions to. During and after her treatment with daptomycin she was able to walk extended distances without her cane and her neurological examination showed improvement as well. The patient reported that daptomycin resulted in a significant decrease in her muscle and nerve pain as well as muscle stiffness, to the extent that she was able to more easily get in an out of a vehicle. The medication also resulted in an increase in strength and sensation of her left upper extremity, which before, felt "dead." After stopping for approximately six weeks, her stiffness had returned but not to the extent as before. More detail about Patient A is provided in Example 3.

Daptomycin is effect in ameliorating muscular sclerosis or the symptoms thereof in patients. The mechanism of action of daptomycin in treating and/or preventing multiple sclerosis is unknown. Without wishing to be bound by theory, daptomycin may alter inflammatory versus counter regulatory cytokine imbalances (interferon gamma or IL-17 versus IL-10 respectively), eliminate aberrant immune responses to Gram positive human microflora, have inhibitory or modulating effects on immune cells, including but not restricted to CD4, CD8, regulatory T cells, macrophages, dendritic cells and/or their function, have neuroprotective effects, including preserving axonal and/or neuron physiology or viability in the setting of inflammation, enhancing the physiological function of partially or completely demyelinated nerves of the central nervous system, or act by some other method.

Following the observation with Patient A, another patient (Patient B) who had almost weekly relapses of her multiple sclerosis stabilized both in terms of the frequency of her relapses and neurological disability after treatment with intravenous daptomycin 4 mg/kg. This is described in more detail in Example 2.

Example 2

Patient B
Brief History of Multiple Sclerosis.
Patient B is a 54 year old woman who was first diagnosed with multiple sclerosis in 1981 at the age of 24. The course of her illness was characterized through the years by increasingly frequent relapses and progressive disability. She had initially been treated with azathioprine and, subsequently with interferons, including Betaseron™ and Avonex®, and Copaxone®. As adjunct treatments, she received innumerable courses of intravenous methylprednisolone, as well as cyclophosphamide, since 2005. In addition, she has also received mycophenylate mofetil, plasma exchange monthly, intravenous immunoglobulin monthly, natalizumab, daclizumab and rituximab. None of these regimens adequately controlled her many relapses, which were characterized by worsening gait and appendicular ataxia, weakness in her limbs, vertigo and diplopia and severe migraine headaches. In late 2008 and 2009, she was hospitalized seven times for relapses. Since 2005, she had received more than 50 courses of steroid and/or cyclophosphamide treatments for relapses not requiring hospitalization. These treatments would induce partial and short lasting remissions. During 2009, she was having relapses on a weekly basis. During remissions, she was able to walk only with a walker.

Daptomycin Treatment
Daptomycin 4 mg/kg intravenously [hereinafter "IV"] was administered to patient B for five days for an acute relapse which made the patient nonambulatory. On the third day, the patient improved to the extent that she was able to walk with her walker. After five days, she was able to take a few steps without her walker in clinic. She did have an allergic reaction with chest tightness and blistering at the injection site that was determined to be caused by the tape securing her IV catheter. She was stable for approximately one week following the initial infusion but then had a recurrence of her ataxia and increased headaches, but not as severe as the previous episode. Daptomycin 4 mg/kg/IV was administered for five additional days with pretreatment with solumedrol in the total amount of 100 mg IV and diphenhydramine in the total amount of 50 mg IV with improvement. Daptomycin was then ordered 4 mg/kg/IV once a week.

Three days after her first weekly dose, she began to feel more off balanced and her headache became more severe. Daptomycin orders were revised to 4 mg/kg IV once a week in co-administration with solumedrol 1 gram IV. Since that time she has been receiving daptomycin at regular intervals with a marked decrease in the frequency of her relapses. Her infrequent relapses respond very rapidly to consecutive courses of daptomycin for three to five days.

Example 3

Patient A
Brief History of Multiple Sclerosis
Patient A is a 53 year old woman who has suffered from multiple sclerosis since age 41. Her disease started with left arm and leg weakness. During the early course of the disease, she experienced frequent relapses. Progressive relapsing continued, with increasing lower extremity weakness. The patient characterized her left arm as feeling like dead weight. Patient A developed diverticulitis in 2006. Her EDSS (Expanded Disability Status Scale) was 5.5 in February, 2007, i.e., patient was able to walk 100 meters without aid or rest; her EDSS was 6.0 by the end of the year, i.e., patient required intermittent or constant assistance with a cane, crutch or brace to walk 100 meters.

During the Course of her Illness, the Patient was Treated with the Following Therapies:
Copaxone® from February to May, 2003: rash
Rebif® from June to October of 2003
Avonex™ from April of 2004 to September, 2004
Started low dose cytoxan and methylprednisolone June of 2004
Cellcept® (mycophenylate mofetil): September, 2004 to September, 2005
Imuran® (azathioprine): September, 2005
IVIG (IV immunoglobulin): September and October of 2006. Discontinued because of severe rash
Different IVIG product tried February, 2007. Rash recurred.
Rituximab® 375 mg/meters squared times two in May and June, 2007. Improvement in left arm; legs more painful. Repeated in December, 2007. Recurrent bronchial infections.
Cytoxan®/MP continued.
May, 2008: c difficile colitis from Valtrex®.
January, 2009: methotrexate 7.5 mg weekly
9 courses of IV solumedrol for relapses between 2005 and 2009.
Daptomycin Treatment
Daptomycin therapy was initiated to treat a MRSA infection after Patient A had knee surgery. She received a daptomycin dose of 100 mg for four weeks. Three months later, she had re-treatment with 500 mg daily for about four weeks.
Course on Daptomycin
Patient A observed a slight improvement in walking after the first daptomycin treatment. This improvement in gait was more immediate and significant after the second treatment. At that point, the patient did not require her cane, but could walk unassisted. Daptomycin therapy was associated with an improvement in muscle pain and stiffness, making it easier for her to get in and out of her car; muscle spasms were reduced and the numbness in her left arm was improved. Symptoms returned somewhat after stopping the therapy, however, the patient was able to maintain walking. Four weeks after discontinuing daptomycin therapy, her EDSS was 2.5 (indicating minimal to mild neurological disability and ambulation not impaired). This represented a significant improvement.

Example 4

Seventeen patients with relapsing remitting (4 patients) and chronic progressive multiple sclerosis (seventeen patients) have received daptomycin therapy at 4 mg/kg IV for periods ranging from five to 21 days. This patient group included Patient A and Patient B from the above examples.

Four out of seventeen patients have received daptomycin for acute relapses, after not responding to, or wishing to be taken of, solumedrol therapy. Three patients reported improvement in their strength and sensation; and one patient stopped therapy because she believed that her sensory symptoms were getting worse while on therapy.

Thirteen patients with chronic progressive multiple sclerosis received daptomycin therapy for symptoms of multiple sclerosis that were progressing, or to improve present symptoms. Nine patients reported better strength. Some patients stopped therapy: one patient, who had chronic severe pain from MS, stopped after one dose because of an increase in pain; another patient, who reported some initial improvement in strength, stopped therapy after being hospitalized for a seizure episode, that was not related to daptomycin therapy; another patient who had initially reported improvement, stopped because he did not feel any subsequent change and was feeling more depressed; and another patient, who noted initial improvement in her leg strength, stopped because of increased fatigue. Three patients noted that daptomycin therapy was associated with significant fatigue. In all chronic progressive patients who report responses to the drug, maintenance doses starting with once a week with or without the addition of intravenous corticosteroids are given. Doses of daptomycin 2 mg/kg are given to patients who report fatigue as a significant side effect.

Overall, in the same study, daptomycin was administered to a total of 30 patients. 14 responded to treatment (47%). Subgroup responses included: secondary progressive MS (SPMS 9/19) (47%; relapsing remitting MS (RRMS 3/6) (50%); RPMS 0/2 (0%); transitional MS (TMS 2/2) (100%); primary progressive MS (PPMS 0/1) (0%). Treatment is ongoing in 11/30 pts (37%). The most common side effect experienced during the course of this therapy was fatigue. Two patients were hospitalized for confusion and increased symptoms. One patient experienced myalgias (muscle pain) with a creatine phosphokinase level (CPK) of 217, indicating mild muscle breakdown, which is a known adverse effect of daptomycin.

Daptomycin was administered as a daily IV infusion at 3 mg/kg, 4 mg/kg or 6 mg/kg as per standard guidelines for 5 to 21 days, then as a maintenance dose of 3 mg/kg, 4 mg/kg or 6 mg/kg once every one to four weeks. Patients were monitored by telephone calls. CPK levels were done as clinically indicated. Patients were selected on the basis of failure or intolerance on other treatments and continued disease activity. The results of these studies are summarized in the following table:

| Init | Age | S | Course | DD yrs | EDSS pretx | EDSS (last) | Prior Therapies | Daptomycin Regimen | Outcome | Status |
|---|---|---|---|---|---|---|---|---|---|---|
| J A | 40 | M | SPMS | 16 | 6.5 | 6.5 | B, C, R, CY, MP, PE, IG, My, | 4 mg/kg × 21 days, then 4 mg/kg q 2 wks | stable. A little more leg strength | A |
| H A | 49 | F | SPMS | 9 | 6 | 6 | B, C, CY, MP, My, PE | 4 mg/kg × 5 days, then 4 mg/kg q 2 wks | slightly dizzy, headaches, benefit unclear | A |
| D B | 53 | F | SPMS | 11 | 6 | 2.5 | C, R, A, C Y, MP, Myc, Az, IG, Rit, MTX | 500 mg IV × 5 weeks, 4 mg/kg × 4 wks, 4 mg/kg q wk | dramatic improvement in left arm strength, pain, spasms, stiffness and gait | A |
| G B | 41 | F | SPMS | 21 | 6.5 | 6.5 | B, A, C, My, CY, MP, IG, Rit, | 4 mg/kg × 21 days. D/Ced p 2½ wks | no benefit in symptoms. Increased pain in extremities | D |
| D E | 48 | M | SPMS | 5 | 6 | 6 | C, MP, CY, PE, OS, R, My, Rit | 4 mg/kg × 5 days, then 4 mg/kg q week | Inc. fatigue and ataxia. | D |
| R F | 48 | M | SPMS | 9 | 4 | 4 | MP, R, PE | 4 mg/kg × 21 days | slightly stronger on tx. Some regression after stopping it. Felt steroids worked better | D |
| C F | 40 | M | TMS | 12 | 6 | 6 | C, MP, CY, R | 4 mg/kg × 21 days | felt stronger but chose not to continue therapy | D |
| L F | 35 | F | RRMS | 11 | 2 | 2.5 | B, MP, C, R, OS, Myc | 4 mg/kg × 5 days (relapse). Repeated 3 mos later (relapse) | 1st relapse: improved; 2nd: temporary improvement | D |
| W F | 55 | F | SPMS | 24 | 6.5 | 6.5 | C, Mit, MP, CY, R, PE, OS, T, My, Dac, IG | 4 mg/kg/day × 14 days (relapse) | initially helped; then recurred on tx. Caused fatigue | D |
| J G | 72 | F | SPMS | 16 | 6.5 | 6.5 | CY, MP, My, A, | 4 mg/kg/day × 21 days, then 4 mg/kg q 2 weeks | stablized condition. Leg strength and endurance improved. | A |
| L G | 53 | F | SPMS | 13 | 6.5 | 6.5 | C, A, MP, Az, CY, MTX, | 4 mg/kg/d × 5 days; 4 mg/kg q 2 wks | feels a little stronger. Nothing worse | A |
| E G | 50 | F | RRMS | 6 | 3.5 | 3.5 | A, OS, MP, My, B, C, CY, | 4 mg/kg/d × 14 days | initially more energy, then severe fatigue | D |
| M G | 54 | M | RPMS | 18 | 6.5 | 6.5 | A, MP, CY, Myc, 2CDA, OS, R, | 4 mg/kg/d × 5 days | no side effects. Felt that walking continued to worsen | D |
| A K | 40 | M | PPMS | 18 | 8.5 | 8.5 | B, A, MP, OS, | 4 mg/kg/d × 15 days, the 4 mg/kg/week | inc strength and dexterity in left hand; voice stronger, benefit transient | D |
| B K | 39 | M | SPMS | 11 | 5.5 | 6 | CY, MP, C, A, B, R, PE, VIG, T, Rit, My | 4 mg/kg/day × 21 days; 4 mg/kg q wk. 6 mg/kg/d times 14 days. | Initially improved, but effect transient. | D |
| J K | 38 | F | SPMS | 4 | 4 | 3.5 | CY, MP, R, B | 4 mg/kg/d × five days (relapse) | No benefit | D |

-continued

| Init | Age | S | Course | DD yrs | EDSS pretx | EDSS (last) | Prior Therapies | Daptomycin Regimen | Outcome | Status |
|------|-----|---|--------|--------|------------|-------------|-----------------|---------------------|---------|--------|
| M K | 54 | F | SPMS | 25 | 6.5 | 6.5 | Az, PE, IG, T, Dac, Rit, C, B, OS, CY, MP, My | 4 mg/kg/d × 5 days (two courses); 4 mg/kg/week | Reduced relapses. Improvement in gait, ataxia, fatigue, headaches, cognition, Mildly inc. CPK | A |
| D L | 41 | M | SPMS | 12 | 7 | 7 | B, CY, MP, PE, 2CDA, R | 4 mg/kg × one dose | significant increase in pain | D |
| R M | 43 | M | RRMS | 7 | 0 | 1 | OS, MP, IG, C | 4 mg/kg/d × 3 days, then 4 mg/kg/week | improved: vision, strength, fatigue; 3rd dose, some dizziness, diplopia, numbness. Tolerating weekly doses. More stable. | A |
| C M | 59 | F | RRMS | 15 | 3 | 3 | A, B, PE, IG, CY | 4 mg/kg/d × 16 days; 4 mg/kg/wk × 4, then 4 mg/kg/q o wk | stablized condition. Vision improved; left hand improved sensation. Felt PE worked better | A |
| D M | 41 | F | RRMS | 15 | 2.5 | 2 | B, C, A Az, MP, OS, CY, PE, R | 4 mg/kg/d × 14 days, then 4 mg/kg/q 1-2 wks | Relpase partially improved. Suppl. Therapy with IVMP; stable. 1 mo good energy. Then lost benefit. | D |
| J O | 50 | F | SPMS | 15 | 6.5 | 6 | A, Mit, C, CY, MP, IG | 4 mg/kg/d × 10 days, then 4 mg/kg/wk | L. side stronger, feels less spastic, fatigue, balance, gait improved, can walk limited distances wo cane | A |
| A P | 42 | F | SPMS | 15 | 6.5 | 6.5 | R, CY, MP, Rit, PE, IG | 4 mg/kg/d × 10 days, then 4 mg/kg/wk | more stamina, standing better, strength improved, gait improved | A |
| J S | 72 | M | SPMS | 6 | 6.5 | 6.5 | CY, MP, PE, B, My, OS, | 4 mg/k/d × 5 days | no significant benefit | D |
| D S | 54 | F | SPMS | 10 | 6 | 6 | CY, MP, My, MTX, R, IG, Rit, | 4 mg/kg/d × 5 days; 2 mg/kg q 2 wks | balance a little better; walking slightly improved; thought she felt on CY/MP. Had significant fatigue on higher dose | A |
| L S | 40 | F | RRMS | 7 | 2.5 | 2.5 | CY, MP, A, R, B, IG, PE, C | 4 mg/kg/day × 5 days | Increased fatigue. Lower extremities might have been stronger | D |

-continued

| Init | Age | S | Course | DD yrs | EDSS pretx | EDSS (last) | Prior Therapies | Daptomycin Regimen | Outcome | Status |
|------|-----|---|--------|--------|------------|-------------|-----------------|--------------------|---------|--------|
| G T | 43 | M | TMS | 23 | 4 | 4 | B, CY, MP, IVIG, My, Rit, | 4 mg/kg/d × 14 days | Initial improvement: balance & gait. Day 14 decreased LOC, rash: hospitalized. Recurrent rash on repeated dose. | D |
| D T | 55 | F | SPMS | 6 | 6.5 | 7 | C, R, MP, CY, My | 4 mg/kg/d × 5 days | Initially stronger, walking improved. 3rd day, mental status changes, vision and gait deterioration. New onset seizures and spasms. | D |
| S T | 49 | M | SPMS | 17 | 6 | 6 | A, C, R, CY, MP, IG, | 4 mg/kg/d × 10 days | Initially some increase in strength, then significant increase in fatigue | D |
| D W | 55 | M | RPMS | 12 | 6 | 6 | Az, B, PE, MP, CY, IG, My, C, Rit | 4 mg/kg/d × 3 days, then 4 mg/kg/week | Initially more dexterity and energy but benefit transient | D |

Table Legend: SPMS—secondary progressive MS; RRMS—relapsing remitting MS; TMS—transitional MS; PPMS—primary progressive MS; RPMS; relapsing progressive MS. STATUS: A = active treatment; D = discontinued treatment. PRIOR THERAPIES: A—Avonex; B—Betaseron; C—Copaxone; R—Rebif; CY—cyclophosphamide; MP—methylprednisolone; PE—plasma exchange; IG—immunoglobulin; My—Cellcept; Aza—azathioprine; Mit—mitoxantrone; OS—oral steroids; 2CDA—cladribine; Rit—rituximab; T—natalizumab; Dac—dacluzumab.

Example 5

Daptomycin and analogs of daptomycin can tested for efficacy in an animal model of MS. In one embodiment, daptomycin is administered orally and the efficacy assessed in an animal model of MS. Models of MS are known in the art, and an exemplary model is described herein below.

Experimental allergic encephalomyelitis (EAE) is induced in 20 female Sprague Dawley (SD) rats by the following procedure, as is previously described (Xiaochang et al., Amelioration of experimental autoimmune encephalomyelitis by BLyS autovaccine, *Vaccine* 26 (2008) 2873-2881; Birnbaum G et al., Heat shock proteins and experimental autoimmune encephalomyelitis (EAE) I. Immunization with a peptide of the myelin protein 2',3' cyclic nucleotide 3' phosphodiesterase that is cross-reactive with a heat shock protein alters the course of EAE. *J. Neurosci. Res.*, 1996, 44:381-96; Kovarik J et al. Immunoregulation and drug treatment in chronic relapsing experimental allergic encephalomyelitis in the Lewis rat. *Int. J. Immunopharmacol.*, 1995, 17:255-63).

The inoculum is composed of a suspension of equal amounts of spinal cord homogenate in 0.9% saline (spinal roots removed) and complete Freund's adjuvant (CFA). SD rats (aged 8 to 10 weeks) are injected with 0.05 ml of the inoculum in each footpad and boosted two weeks later with the same volume of inoculum. Scoring for neurological deficits is carried out in a blinded fashion as described in Kalyvas A, David S. Cytosolic phospholipase A2 plays a key role in the pathogenesis of multiple sclerosis-like disease. Neuron 2004; 41:323-35) as follows: grade 1, flaccid tail; grade 2, mild hindlimb weakness; grade 3, severe hindlimb weakness; grade 4, hindlimb paralysis; grade 5, hindlimb paralysis and forelimb weakness or moribund. The onset of EAE is the day on which a rat scores 1 for the first time.

Ten rats each in control and test groups are administered (by oral gavage) a delivery agent compound 4-(6-(2-hydroxyphenoxy)hexyl)morpholinium citrate alone (control), or with daptomycin (test). Daptomycin is administered in the dose of 50 mg/kg on day #1 of EAE onset. Daily scores are tabulated until the animals are sacrificed at 21 days from the start of trial for sectioning and histopathology. Rats are anaesthetized with pentobarbital (80 mg/kg) and 2 ml blood is collected from the heart. A 0.9% saline solution is perfused through the left ventricle, and is followed by perfusion of 500 ml of 10% formaldehyde in 0.1 M phosphate buffer (PB) 500 ml at pH 7.4. The cerebellum and spinal cord are removed and preserved in a fixative. Slices of fixed tissue are embedded in paraffin wax and sliced in 5 μm sections and 10 μm sections, the latter for frozen sectioning. The sections are stained with hematoxylin-eosin (HE) and Luxol fast blue following standard staining procedures. The sections are observed under a light microscope for areas of demyelination. The results are observed and recorded.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating multiple sclerosis in a subject comprising administering to the subject a composition comprising an effective amount of at least one of the following: daptomycin or a pharmaceutically acceptable salt thereof.

2. The method of claim 1, wherein the composition is administered intravenously.

3. The method of claim 2, wherein daptomycin is administered at a dose of 4 mg/kg or 6 mg/kg.

4. The method of claim 1, wherein the composition is administered orally.

5. The method of claim 1, wherein the composition is administered for a duration sufficient to ameliorate multiple sclerosis or symptoms associated with multiple sclerosis.

6. The method of claim 5, wherein the duration is daily for 1-6 weeks.

7. The method of claim 5, wherein the duration is daily for 1-6 months.

8. A method of ameliorating multiple sclerosis or symptoms associated with multiple sclerosis in a subject identified as in need of treatment, the method comprising administering to a human subject in need thereof a composition comprising an effective amount of at least one of the following: daptomycin or a pharmaceutically acceptable salt thereof.

9. The method of claim 8, wherein the composition is administered intravenously.

10. The method of claim 9, wherein daptomycin is administered at a dose of 4 mg/kg or 6 mg/kg.

11. The method of claim 8, wherein the composition is administered orally.

12. The method of claim 8, wherein the composition is administered for a duration sufficient to ameliorate multiple sclerosis or symptoms associated with multiple sclerosis.

13. The method of claim 12, wherein the duration is daily for 1-6 weeks.

14. The method of claim 12, wherein the duration is daily for 1-6 months.

15. A method of treating multiple sclerosis, or symptoms associated with multiple sclerosis, in a human subject identified as in need of such treatment, the method comprising administering to the human subject a composition comprising an effective amount of daptomycin, or a pharmaceutically acceptable salt thereof, wherein the effective amount is selected from the group consisting of 3 mg/kg, 4 mg/kg, and 6 mg/kg.

* * * * *